(12) United States Patent
Halonen et al.

(10) Patent No.: US 6,245,819 B1
(45) Date of Patent: Jun. 12, 2001

(54) METHOD FOR THE TREATMENT OF VAGINAL DRYNESS AND SEXUAL DYSFUNCTION IN WOMEN DURING OR AFTER THE MENOPAUSE

(75) Inventors: Kaija Halonen, Rusko; Lauri Kangas, Raisio, both of (FI); Michael W. DeGregorio, Granite Bay, CA (US)

(73) Assignees: Hormos Medical Oy, Ltd. (FI); Tess Diagnostics and Pharmaceuticals, Inc., Granite Bay, CA (US)

( * ) Notice: Subject to any disclaimer, the term of this patent is extended or adjusted under 35 U.S.C. 154(b) by 0 days.

(21) Appl. No.: 09/625,199

(22) Filed: Jul. 21, 2000

(51) Int. Cl.[7] .................................................. A61K 31/075
(52) U.S. Cl. .............................................................. 514/721
(58) Field of Search ............................................ 514/721

(56) References Cited

U.S. PATENT DOCUMENTS

| | | |
|---|---|---|
| 5,750,576 | 5/1998 | DeGregorio et al. . |
| 5,912,273 | 6/1999 | Degregorio et al. . |
| 6,037,379 | 3/2000 | Harkonen et al. . |

OTHER PUBLICATIONS

Baynes, K.C.R. and Compston, J.E. (1998). "Selective oestrogen receptor modulators: a new paradigm for HRT." *Curr. Opin. Obstetrics Gynecology* 10:189–192.

DeGregorio, M.W. and Taras, T.L. (1998). "Hormone replacement therapy and breast cancer: revisiting the issues." *J. Am. Pharm. Assoc.* 38:738–746.

Kangas, L. (1990). Biochemical and pharmacological effects of toremifene metabolites.: *Cancer Chemother. Pharmacol.* 27:8–12.

Kennedy, M.M. et al. (1999). "Tamoxifen and the endometrium: review of 102 cases and comparison with HRT–related and non–HRT–related endometrial pathology." *Int'l. J. Gynecological Patholoy* 18:130–137.

Whitehead, M. (1996). "Treatments for menopausal and post–menopausal problems: present and future." *Bailliere's Clin. Obstetrics Gynaecology* 10:515–530.

*Primary Examiner*—Raymond Henley, III
(74) *Attorney, Agent, or Firm*—Rothwell, Figg, Ernst & Manbeck, p.c.

(57) ABSTRACT

This invention concerns a method for the treatment of vaginal dryness or sexual dysfunction in women during or after the menopause, said method comprising administering to the woman an effective amount of the compound (deaminohydroxy)toremifene or a pharmaceutically acceptable salt or ester thereof, or a metabolite thereof.

6 Claims, 3 Drawing Sheets

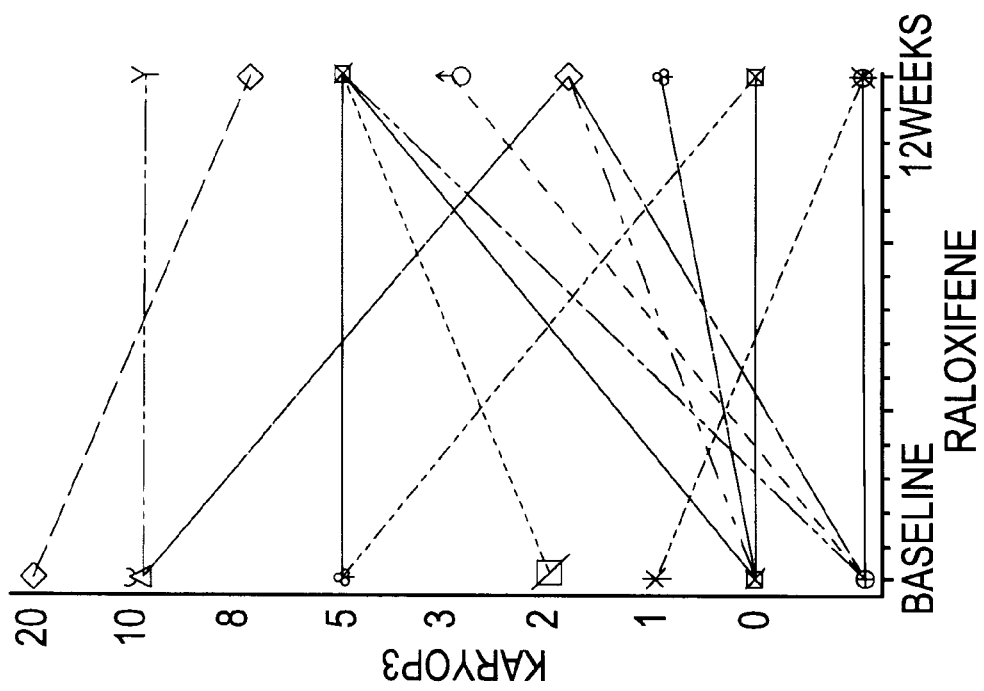

METHOD FOR THE TREATMENT OF VAGINAL DRYNESS AND SEXUAL DYSFUNCTION IN WOMEN DURING OR AFTER THE MENOPAUSE

FIELD OF THE INVENTION

This invention relates to a method for the treatment of vaginal dryness or sexual dysfunction in women during or after menopause.

BACKGROUND OF THE INVENTION

The publications and other materials used herein to illuminate the background of the invention, and in particular, cases to provide additional details respecting the practice, are incorporated by reference.

During and after menopause, elderly women commonly develop symptoms which are due to estrogen deficiency. These symptoms include hot flashes, sweating, insomnia, depression, vaginal dryness, urinary incontinence, nausea, pain, osteoporosis, coronary heart disease, breast tenderness, oedema, fatigue, decreased sexual activity, as well as subsequent psychosocial problems (Payer, 1990; Rekers, 1990). In addition, estrogens are suggested to have neuroprotective effects. Thus, declining estrogen concentrations may negatively affect the mental activities of aging women (Schneider & Finch, 1997; Wickelgren, 1997). Estradiol is known to be excellent in the treatment of climacteric symptoms, and its use in the treatment of these symptoms is rapidly increasing. However, estrogens cause an increased risk of endometrial and breast cancers. It is possible to decrease the carcinogenicity of endometrial cancer by sequential progestin administration, but the risk of breast cancer is not diminished by progestins. The carcinogenicity risk limits the length of estrogen replacement therapy, although it would be very useful to continue the therapy long term, due to the protective effects of estrogens in the bone, in the cardiovascular system, in the central nervous system, and for urinary symptoms.

Antiestrogens, now often referred to as "SERM"s (selective estrogen receptor modulators), have both estrogen-like and antiestrogenic properties (Kauffman & Bryant, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. Based on the published information, all SERMs are more likely to cause menopausal symptoms than to prevent them. They have, however, other important benefits in elderly women: they decrease total and LDL cholesterol, thus deminishing the risk of cardiovascular diseases, and they may prevent osteoporosis and inhibit breast cancer growth in postmenopausal women. There are also almost pure antiestrogens under development. They are mainly aimed at the treatment of breast cancer (Wakeling & Bowler, 1988).

The compound (deaminohydroxy)toremifene, which also is known under the code FC-1271 a, has relatively weak estrogenic and antiestrogenic effects in the classical hormonal tests (Kangas, 1990). It has antiosteoporosis actions and it decreases total and LDL cholesterol levels in both experimental models and in human volunteers (International patent publications WO 96/07402 and WO 97/32574). It also has antitumor activity in an early stage of breast cancer development in an animal breast cancer model. The effect of antiestrogens on climacteric symptoms has not been studied earlier. FC-1271 a is the first SERM which has been shown to have beneficial effects in age-related syndromes in healthy women.

SUMMARY OF THE INVENTION

The invention concerns a method for the treatment of vaginal dryness or sexual dysfunction in women during or after the menopause, said method comprising administering to the woman an effective amount of the compound (deaminohydroxy)toremifene or a pharmaceutically acceptable salt or ester thereof, or a metabolite thereof.

BRIEF DESCRIPTION OF THE DRAWINGS

FIGS. 1A to 1D show changes (from start to 12 weeks' treatment) in the karyopyknosis index for superficial cells of the vaginal epithelium for the individuals treated daily with 30 mg FC-1271a (1A), 60 mg FC-1271a (1B), 90 mg FC-1271 a (1C), and 60 mg raloxifene (1D).

DETAILED DESCRIPTION OF THE INVENTION

Figure 1B:
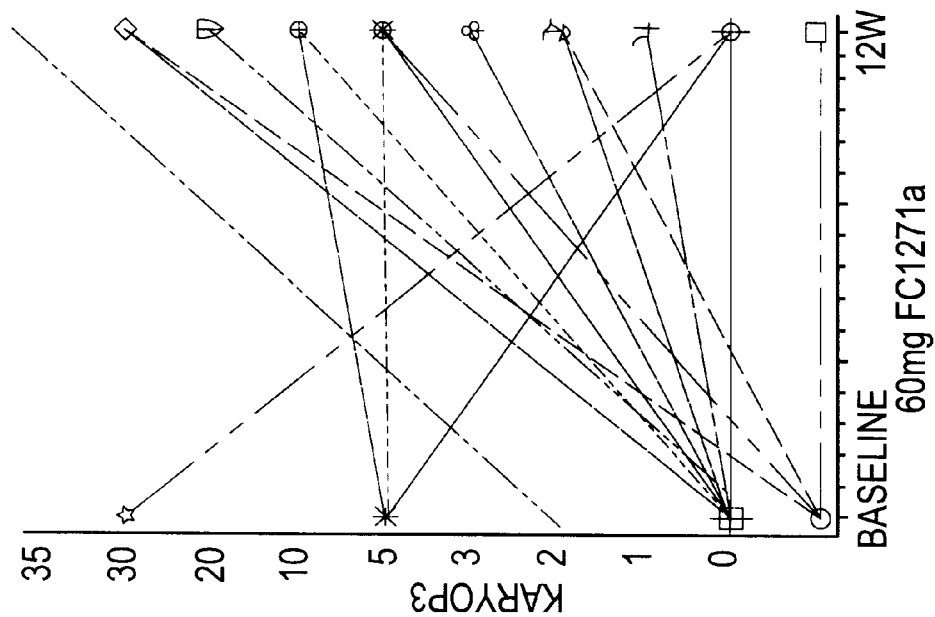
Figure 1A:
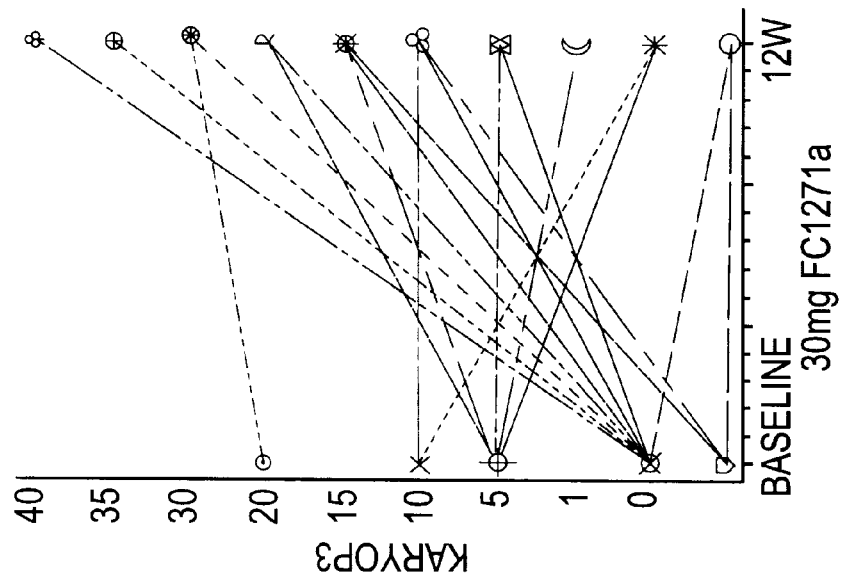

This invention relates to the use of the estrogen receptor modulator FC-1271 a, (deaminohydroxy)toremifene, in elderly women suffering from vaginal dryness or sexual dysfunction. FC-1271 a, one of the main metabolites of toremifene, is known to be an estrogen agonist and antagonist (Kangas, 1990; International patent publications WO 96/07402 and WO 97/32574).

The formula of FC-1271 a (or (deaminohydroxy) toremifene) is

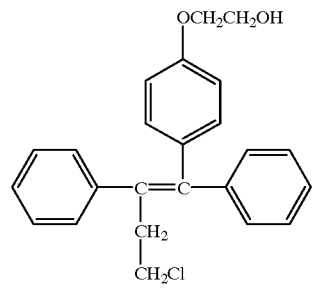

The compound shall be understood to also include its geometric isomers and stereoisomers.

The term "metabolite" shall be understood to cover any (deaminohydroxy)toremifene metabolite already discovered or to be discovered. As examples of such metabolites can be mentioned the oxidation metabolites mentioned in Kangas (1990) on page 9 (TORE VI, TORE VII, TORE XVIII, TORE VIII, TORE XIII), especially TORE VI and TORE XVIII, and other metabolites of the compound.

The new and surprising effect of this compound was found in a clinical study. In this study, raloxifene (60 mg/day) or FC-1271a at different doses were given to elderly female volunteers for a period of 3 months. At the dose levels of 30, 60 and 90 mg daily, a significant decrease in vaginal dryness was observed. An improved sexual activity was also reported. These properties are new and unique among the known selective estrogen receptor modulators (SERMs) and indicate that FC-1271a at the doses from 25 mg to slightly lower than 100 mg daily, particularly 30 to 90 mg daily, can be successfully used to alleviate vaginal dryness and sexual dysfunction of elderly women. Furthermore, FC-1271 a has a superior profile of estrogenic and antiestrogenic effects when compared to any known antiestrogen or SERM compound.

The compound FC-1271 a has been found to alleviate sexual dysfunction and to increase the sexual activity. Types and causes of female sexual dysfunction are 1) Desire disorders, 2) Arousal disorders, 3) Orgasmic disorders and 4) Painful intercourse (dyspareunia). Most of these are due to hormonal reasons, especially to reduced estrogen and testosterone concentrations. Vaginal dryness is one of the main causes of female sexual dysfunction and will typically develop after the menopause when the estrogen concentrations decrease. Typically this leads to painful intercourse, which indirectly may influence on any type of sexual dysfunction, including psychological causes. In elderly women vaginal dryness is often the main reason for decreased sexual activity. (Spector I P, Carey M P: Incidence and prevalence of sexual dysfunctions: a critical review of the empirical literature. Archives of Sexual Behaviour 19: 389–408, 1990).

Estrogens and testosterone are useful pharmaceutical treatments of vaginal dryness and it is not surprising that pure antiestrogens like raloxifene cause vaginal dryness. Subsequently, the patients are not satisfied with the treatment which causes painful intercourse and will stop the therapy.

The compound can be administered by various routes of which oral or transdermal administration routes are the most preferable.

Suitable preparation forms include for example tablets, capsules, granules, powders, suspensions, syrups and transdermal ointments or gels.

Experiments

A clinical phase I–II study was carried out to study the effects of FC-1271a on endometrial thickness, endometrial pathology, (biopsy taken by curettage as described by Vuopala et al, 1982) and cervical smear in healthy postmenopausal female volunteers in the age range 55 to 69 years. Tolerability and pharmacokinetics were also assessed. Raloxifene (60 mg daily) was used as reference. FC-1271 a was given perorally at the doses of 30, 60 and 90 mg daily. There were 29 volunteers at each dose level, as well as in the raloxifene group. FC-1271a was administered in gelatine capsules containing either 30, 60 or 90 mg of FC-1271 a. The thickness of the endometrium was evaluated by ultrasonography using a Hitachi EUB-405 instrument. The vaginal epithelium was assessed by karyopyknosis index which is a well known assessment method among the skilled persons. In this method, the vaginal fraction of the cervical smears is estimated as the percentage of the number of cells from different layers: the parabasal cell layer; the intermediate cell layer; and the superficial cell layer. Estrogenicity is seen by a shift towards superficial cell fraction. In postmenopausal women this fraction usually is close to zero and estradiol treatment increases the fraction close to 100. Samples were taken before and after the treatment (at 3 months).

The vaginal dryness symptoms were also assessed by using a visual analogue scale where the volunteers themselves recorded their subjective estimates. The scale is based on a 100-mm line on paper. The left end represents no symptom and the right end the worst possible symptom. The change from pretreatment to 3 months estimates was assessed and considered to be indicative of the treatment efficacy.

There were no differences in the demographic data between the treatment groups in any of the pretreatment measurements.

Assessment of the vaginal estrogenic effect of FC-1271a

Table 1 below shows the change in maturity index for parabasal cells (MI 1) and maturity index for superficial cells (MI 3), after 3 months' administration of varying doses of FC-1271a or raloxifene.

TABLE 1

Change in maturity index for parabasal cells (MI 1) and maturity index for superficial cells (MI 3), after 3 months' administration of varying doses of FC-1271a or raloxifene. (MI 1: index 100 no estrogenicity; index 0 full estrogen, and MI 3: index 100 full estrogen; index 0 no estrogenicity).

| Compound and dose | MI 1 mean | MI 1 Sd | MI 3 mean | MI 3 sd |
|---|---|---|---|---|
| FC-1271a, 30 mg, (n = 21) | −40 | 42 | +12.4 | 13.6 |
| FC-1271a, 60 mg, (n = 20) | −26 | 39 | +5.5 | 13.4 |
| FC-1271a, 90 mg, (n = 22) | −48 | 44 | +12.5 | 14.0 |
| Raloxifene, 60 mg, (n = 19) | −2 | 34 | −0.3 | 4.1 |

In FIGS. 1A to 1D there are shown changes (from start to 12 weeks' treatment) in the karyopyknosis index for superficial cells of the vaginal epithelium for the individuals treated daily with 30 mg FC-1271a (1A), 60 mg FC-1271a (1B), 90 mg FC-1271a (1C), and 60 mg raloxifene (1D).

Cervical smear assessments indicate that no one in the raloxifene group (FIG. 1D) had a significant change from baseline to postreatment in the karyopyknosis index for superficial cells. Most of the individuals in the FC-1271a groups had slight increases in the index, but in other subjects the estrogenic effect was very weak, if measurable at all. In all cases the increase was small (<40 except for one case which was 45 in the 90 mg group) when compared to estradiol which is known to increase the index virtually by 100. A weak but statistically significant estrogenic effect in the cervical smear was therefore documented. No pathological changes were seen in any sample.

Figure 2:
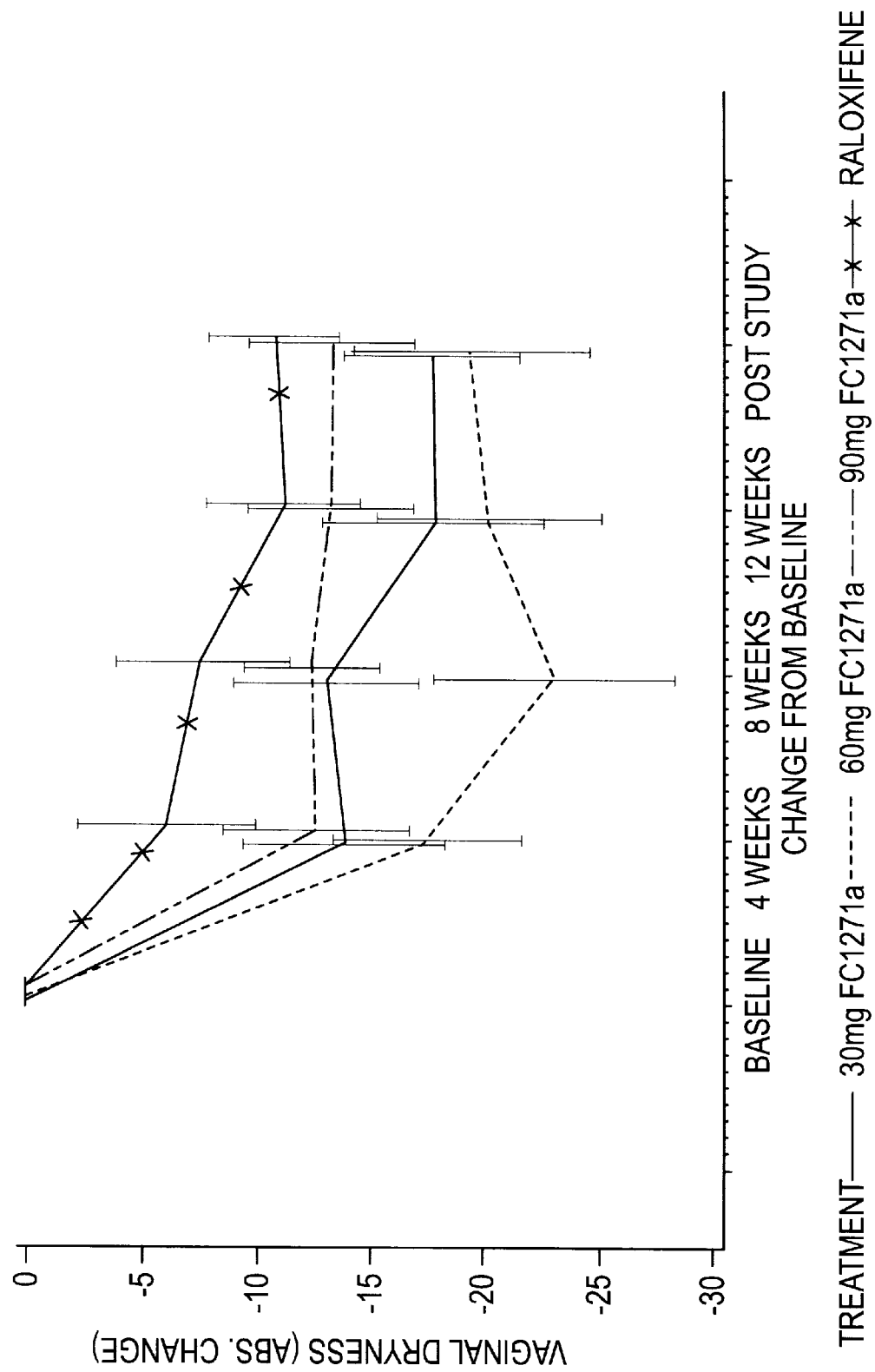
FIG. 2 shows the effect of 30 mg, 60 mg and 90 mg daily doses of FC-1271a and raloxifene (daily dose 60 mg) on vaginal dryness, assessed as the individuals' subjective estimates.

FIG. 2 shows that raloxifene caused only a minor decrease on vaginal dryness, assessed by the individuals' subjective estimate, while all the FC-1271a dosage levels indicated a clear decreasing effect. The dose level 60 mg FC-1271a daily gave the best result.

Assessment of the Endometrial Estrogenic Effect of FC-1271a

FC-1271a had a weak estrogenic effect on endometrial histology. This effect is clearly weaker than that seen with estrogen replacement therapy. There were no malignant findings in the endometrium. The thickness of the endometrium as assessed by ultrasonography showed only a minor, statistically not significant, increase in the thickness (average 0.2 mm, 0.5 mm and 0.5 mm) at the dose levels of 30, 60 and 90 mg, respectively. The measured values were always smaller than 8 mm, which is considered to be a thickness which is indicative for a physiologically significant estrogenicity of antiestrogenic drugs like tamoxifen (Hann et al, 1997; Lahti et al, 1993).

Effect on Sexual Activity

In the clinical study, where the effects of FC-1271 a on quality of life and cardiovascular parameters were studied, the patients were asked for sexual activity. The questionnaire included "worsening" or "no effect" on sexual activity. Improvement on sexual activity was not asked. When 70 patients had been followed up for 6 weeks, 27 of them had spontaneously reported to the investigators increased sexual activity. Similar reports were independently obtained from different centers of the study. This strongly suggests that FC-1271a has a positive effect on the sexual activity and quality of life.

The results indicate that FC-1271 a has a unique pharmacological profile with regard to estrogen-like effects on vaginal dryness and insignificant endometrial effects. In the clinical study, FC-1271 a has a weak estrogen-like activity in the vagina and uterus. In these tissues the estrogenicity is markedly lower than that of the known antiestrogens tamoxifen and toremifene, but higher than that of raloxifene. In contrast to other antiestrogens, it does not cause menopausal symptoms. Actually FC-1271a at the doses of 25 mg or more, and especially 30–90 mg daily, alleviated such symptoms. FC-1271a has an especially beneficial effect in that it decreases vaginal dryness and sexual dysfunction. Based on the present data, the optimal clinical dose is expected to be higher than 25 mg daily and lower than 100 mg daily. A particularly preferable daily dose is found in the range 30 to 90 mg. At the higher doses (100 and 200 mg daily), FC-1271a shows more antiestrogen-like properties and behaves almost like tamoxifen and toremifene. FC-1271a is an especially valuable drug because it has an excellent tolerability. In addition, FC-1271a decreases total and LDL cholesterol, increases HDL cholesterol, and prevents osteoporosis and early stage breast cancer. The present invention suggests that FC-1271a can be also used during menopause as hormone replacement therapy instead of estrogens, which are known to increase the risk of breast and endometrium cancers.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Delmas P D, Bjarnason N H, Mitlak B H, Ravoux A C, Shah A S, Huster W J, Draper M, Christiansen C: Effects of raloxifene on bone mineral density, serum cholesterol concentrations, and uterine endometriun in postmenopausal women. N Engl J Med 337: 1641–1647, 1997

Ettinger B, Genant H K, Cann C E: Long-term estrogen replacement therapy prevents bone loss and fractures. Ann Intern Med 102: 319–324, 1985

Hann L E, Giess C S, Bach A M, Tao Y, Baum H J, Barakat R R: Endometrial thickness in tamoxifen-treated patients: correlation with clinical and pathologic findings. Am J Roentgenol 168: 657–661, 1997

Gustafsson J-Å: Estrogen receptor β—getting in on the action? Nature Medicine 3: 493–494, 1997

Kangas L: Biochemical and pharmacological effects of toremifene metabolites. Cancer Chemother Pharmacol 27: 8–12, 1990

Kauffman R F, Bryant H U: Selective estrogen receptor modulators. Drug News Perspect 8: 531–539, 1995

Lahti E, Blanco G, Kauppila A, Apaja-Sarkkinen M, Taskinen P J, Laatikainen T: Endometrial changes in postmenopausal breast cancer patients receiving tamoxifen. Obstet Gynecol 81: 660–664, 1993

Palkowitz A D, Glasebrook A L, Thraser K J, Hauser K L, Short L L, Phillips D L, Muchi B S, Sato M, Shetler P K, Cullinan G J, Pell T R, Bryant H U: Discovery and synthesis of [6-hydroxy-3-[4-[2-(1 -peridinyl)ethoxy] phenoxy]-2-(4-hydroxyphenyl)]benzo[b]thiophene: a novel, highly potent, selective estrogen receptor modulator. Med Chem 40: 1407–1416, 1997

Payer L: The menopause in various cultures. In: A portrait of the menopause. Expert reports on medical and therapeutic strategies for the 1990s. Ed. Burger H & Boulet M, Parthenon Publishing, Park Ridge, N.J., USA, 1991. pp 3–22

Rekers H: Matering the menopause. In: A portrait of the menopause. Expert reports on medical and therapeutic strategies for the 1990s. Ed. Burger H & Boulet M, Parthenon Publishing, Park Ridge, N.J., USA, 1991. pp 23–43

Schneider L S, Finch C E: Can estrogens prevent neurodegeneration. Drugs & Aging 11: 87–95, 1997

Spector I P, Carey M P: Incidence and prevalence of sexual dysfunctions: a critical review of the empirical literature. Archives of Sexual Behaviour 19: 389–408, 1990.

Vuopala S, Kauppila A, Mikkonen M, Stenbäck F: Screening of asymptomatic postmenopausal women for gynecological malignancies, with special reference to endometrial sampling methods. Arch Gyncol 231: 119–127, 1982

Wakeling A E, Bowler J: Biology and mode of action of pure antiestrogens. J Steroid Biochem 30: 1–6, 1988

Wickelgren I: Estrogen stakes claim to cognition. Science 276: 675–678, 1997

What is claimed is:

1. A method for the treatment of vaginal dryness or sexual dysfunction in women during or after the menopause, said method comprising administering to the woman an effective amount of the compound (deaminohydroxy)toremifene or a pharmaceutically acceptable salt or ester thereof or metabolite thereof.

2. The method according to claim 1 wherein the compound or its salt or ester is administered in a daily dose varying in the range of 25 to 100 mg.

3. The use according to claim 2 wherein the compound or its salt or ester is administered in a daily dose varying in the range of 30 to 90 mg.

4. The method according to claim 1 wherein the compound or its salt or ester is administered orally or transdermally.

5. The method according to claim 2 wherein the compound or its salt or ester is administered orally or transdermally.

6. The method according to claim 3 wherein the compound or its salt or ester is administered orally or transdermally.

* * * * *

UNITED STATES PATENT AND TRADEMARK OFFICE
CERTIFICATE OF CORRECTION

PATENT NO. : 6,245,819 B1
APPLICATION NO. : 09/625199
DATED : June 12, 2001
INVENTOR(S) : Kaija Halonen et al.

Page 1 of 1

It is certified that error appears in the above-identified patent and that said Letters Patent is hereby corrected as shown below:

In the Claims

In column 6, claim 3, line 48, before "according to" replace "The use" with --The method--.

Signed and Sealed this
Twenty-seventh Day of May, 2014

Michelle K. Lee
*Deputy Director of the United States Patent and Trademark Office*